US012714462B2

(12) United States Patent
Pilletere et al.

(10) Patent No.: US 12,714,462 B2
(45) Date of Patent: Aug. 25, 2026

(54) VALVE ASSEMBLY AND RETAINER FOR SURGICAL ACCESS ASSEMBLY

(71) Applicant: Covidien LP, Mansfield, MA (US)

(72) Inventors: Roy Pilletere, Middletown, CT (US); Jacob Baril, Norwalk, CT (US); Garrett Ebersole, Hamden, CT (US); Matthew Dinino, Newington, CT (US); Justin Thomas, New Haven, CT (US); Eric Brown, Madison, CT (US); Nicolette LaPierre, Windsor Locks, CT (US)

(73) Assignee: Covidien LP, Mansfield, MA (US)

( * ) Notice: Subject to any disclaimer, the term of this patent is extended or adjusted under 35 U.S.C. 154(b) by 127 days.

(21) Appl. No.: 18/901,613

(22) Filed: Sep. 30, 2024

(65) Prior Publication Data

US 2025/0017621 A1 Jan. 16, 2025

Related U.S. Application Data

(60) Continuation of application No. 17/839,865, filed on Jun. 14, 2022, now Pat. No. 12,127,762, which is a division of application No. 16/448,654, filed on Jun. 21, 2019, now Pat. No. 11,357,542.

(51) Int. Cl.

| | |
|---|---|
| ***A61B 17/34*** | (2006.01) |
| ***F16K 13/02*** | (2006.01) |
| *F16K 99/00* | (2006.01) |

(52) U.S. Cl.

CPC .......... *A61B 17/3423* (2013.01); *F16K 13/02* (2013.01); *A61B 2017/3441* (2013.01); *A61B 2017/3445* (2013.01); *A61B 2017/345* (2013.01); *F16K 2099/0086* (2013.01)

(58) Field of Classification Search

CPC ...... A61B 2017/345; A61B 2017/3441; A61B 2017/3445; A61B 2017/3464; A61B 2017/3466; A61B 17/3462; A61B 17/3423; F16K 2099/0086; F16K 13/02

See application file for complete search history.

(56) References Cited

U.S. PATENT DOCUMENTS

| | | | | |
|---|---|---|---|---|
| 2008/0294112 A1* | 11/2008 | Judson ............... | A61B 17/3462 604/167.06 |
| 2015/0216560 A1* | 8/2015 | Holsten ............. | A61B 17/3462 600/204 |
| 2018/0021063 A1* | 1/2018 | Main ................. | A61B 17/3474 604/167.01 |
| 2018/0085145 A1* | 3/2018 | Okoniewski ....... | A61B 17/3462 |

OTHER PUBLICATIONS

File history of parent application, U.S. Appl. No. 17/839,865, 125 pgs.
File history of parent application, U.S. Appl. No. 16/448,654, 179 pgs.

* cited by examiner

*Primary Examiner* — Tuan V Nguyen
(74) *Attorney, Agent, or Firm* — Dymera IP, LLC

(57) ABSTRACT

A surgical access assembly includes a cannula, a valve housing attached to the cannula, and a valve assembly positioned in the valve housing. The valve assembly includes a centering mechanism with a hoop and fingers, a ring with a flange at one end of the ring, a retainer having first and second discs, a guard having a frame and flaps attached to the frame, and a seal with petals attached to a support. The guard is at least partially disposed in the first disc and the seal is at least partially disposed in the second disc.

17 Claims, 12 Drawing Sheets

165d
164d 167d
161d 163d
162d 169d 166d 173d
163c
165e 166e 169e
167c
164c
160
162e
173e
161c
173c
169c
161e
167e
166c
164e
163e
162c
172d
175d
172e
172c
165c
175c
175e
178
12
165f
172b
163b
175f
169f
170
175b
162b
172f
162f
164b
176
172a
176
166f
175a
167b
173f
173b
161b
161f
166b
167f
12
165b
164f
169b
163f
163a
162a
164a
167a
173a
161a
169a
166a
165a

VALVE ASSEMBLY AND RETAINER FOR SURGICAL ACCESS ASSEMBLY

CROSS-REFERENCE TO RELATED APPLICATION

This application is a continuation of U.S. patent application Ser. No. 17/839,865, filed Jun. 14, 2022, which is a division of U.S. patent application Ser. No. 16/448,654, filed on Jun. 21, 2019, now U.S. Pat. No. 11,357,542, the entire contents of which are hereby incorporated by reference.

FIELD

The present disclosure relates to assemblies including seals for minimally invasive surgery. More particularly, the present disclosure relates to valve assemblies and retainers for surgical access assemblies.

BACKGROUND

In order to facilitate minimally invasive surgery, a working space must be created at a surgical site. An insufflation fluid, typically $CO_2$, is introduced into the abdomen of the patient to create an inflated state called pneumoperitoneum. Surgical access assemblies are utilized to allow the introduction of surgical instrumentation and endoscopes (or other visualization tools). These surgical access assemblies maintain the pressure for the pneumoperitoneum, as they have one or more seals that adapt to the surgical instrumentation. Typically, a “zero-seal” in the surgical access assembly seals the surgical access assembly in the absence of a surgical instrument in the surgical access assembly, and an instrument seal seals around a surgical instrument that has been inserted through the surgical access assembly.

The breadth of surgical instrumentation on the market today requires a robust seal capable adjusting to multiple sizes and withstanding multiple insertions and withdrawals of surgical instrumentation. Some of the surgical instrumentation can include sharp edges that can tear or otherwise damage seals.

In addition to the instrument seal, a valve assembly also includes a guard and a centering mechanism. The guard helps minimize damage to the instrument seal during insertion and withdrawal of a surgical instrument through the valve assembly. A retainer is often used to maintain the position and alignment of the various components used in the valve assembly. The retainer may have multiple components that use posts and holes to join them together. As the posts need to extend through the various components in the valve assembly, the posts may also increase the assembly time of the valve assembly. A retainer without posts and corresponding holes would be beneficial.

SUMMARY

In embodiments, a surgical access assembly includes a cannula, a valve housing coupled to a proximal end of the cannula, and a valve assembly disposed in the valve housing. The valve assembly includes a centering mechanism, a ring, a retainer, a guard, and a seal. The centering mechanism includes a hoop having fingers extending radially outwards from an outer surface of the hoop. Each finger is flexibly connected to the outer surface and biased away from the outer surface. The ring has an outer diameter and a flange disposed at one end of the ring. The other end of the ring abuts one end of the hoop. The retainer has a first disc disposed in the ring and a second disc disposed in the hoop. The first disc is attachable to the second disc irrespective of the rotational orientation of the first disc relative to the second disc. The guard includes a frame and flaps flexibly coupled thereto. The guard is partially disposed in the first disc. The seal includes petals flexibly coupled to a support and the seal is partially disposed in the second disc.

The first disc may include a channel adapted to receive a portion of the frame and the second disc may include a groove adapted to receive a portion of the support. The second disc may include receptacles configured to receive protrusions of a plate.

One of the first or second discs may include a ridge circumscribing a central opening thereof and the other of the first or second discs may include a slot circumscribing a central opening thereof. The ridge may be adapted to fit within the slot for coupling the first and second discs together.

The first disc may be secured to the second disc. The first disc may be welded to the second disc.

In embodiments, a valve assembly for use in a surgical access assembly includes a guard, a seal, a centering mechanism, and a retainer. The guard includes a frame and flaps flexibly coupled thereto. The seal includes a support and petals flexibly coupled thereto. The centering mechanism includes a hoop and fingers. The fingers have first and second ends. The first ends of the fingers are flexibly coupled to an outer surface of the hoop and the second ends of the fingers are biased away from the outer surface. The retainer has first and second discs. The first disc has a ridge and the second disc has a slot configured to receive the ridge therein. One of the first or second discs is positionable in a passage defined by the hoop.

The valve assembly may be positionable in a housing of a surgical access assembly.

The first disc of the retainer may be securable to the second disc of the retainer irrespective of their relative angular orientations.

The valve assembly may include a plate disposed between the seal and the second disc.

The plate may include protrusions and the second disc may include receptacles for receiving the protrusions of the plate.

The guard and the seal may be located between the first and second discs of the retainer.

The valve assembly may include a ring abutting the hoop and the ring may be configured to receive the other of the first or second discs therein.

In embodiments, a surgical access assembly includes a valve housing, a cannula extending from the valve housing, and a valve assembly disposed in the valve housing. The valve assembly has a centering mechanism, a guard with a frame and flaps coupled to the frame, a seal with a support and petals coupled to the support, and a retainer including first and second discs. The centering mechanism has a hoop and fingers extending radially from the hoop. The guard is disposed on a first side of the centering mechanism and the seal is disposed on a second side of the centering mechanism. The guard is coupled to the first disc in a fixed orientation and the seal is coupled to the second disc in a fixed orientation. The first disc is attachable to the second disc irrespective of the rotational orientation of the first disc relative to the second disc.

The first disc may include a ridge and the second disc may include a slot for receiving the ridge therein. The first and second discs may be secured to one another. The first and second discs may be welded together.

The first disc may include a channel adapted to receive a portion of the frame and the second disc may include a groove adapted to receive a portion of the support.

BRIEF DESCRIPTION OF DRAWINGS

Embodiments of an instrument seal are disclosed herein with reference to the drawings, wherein.

DETAILED DESCRIPTION

Embodiments of the presently disclosed instrument seal for a surgical access assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Surgical access assemblies are employed during minimally invasive surgery, e.g., laparoscopic surgery, and provide for the sealed access of surgical instruments into an insufflated body cavity, such as the abdominal cavity. The surgical access assemblies of the present disclosure include a valve housing mounted on a cannula tube, and include an obturator (not shown) inserted through the valve housing and cannula tube. The obturator can have a blunt distal end or a bladed or non-bladed penetrating distal end and can be used to incise the abdominal wall so that the surgical access assembly can be introduced into the abdomen. The handle of the obturator can engage or selectively lock into the valve housing of the surgical access assembly.

Surgical access assemblies with a trocar obturator are employed to tunnel through an anatomical structure, e.g., the abdominal wall, either by making a new passage through the structure or by passing through an existing opening through the anatomical structure. Once the surgical access assembly with the trocar has tunneled through the anatomical structure, the trocar obturator is removed, leaving the surgical access assembly in place. The valve housing of the surgical access assembly includes valves that prevent the escape of insufflation fluid from the body cavity, while also allowing surgical instruments to be inserted into the cavity and minimizing the escape of insufflation fluid.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of the obturator. The bladeless obturator may be provided for the blunt dissection of the abdominal lining during a surgical procedure.

Various trocar obturators suitable for use with the surgical access assemblies of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905 ("the '905 publication"), the content of which is hereby incorporated by reference herein in its entirety.

Figure 1:
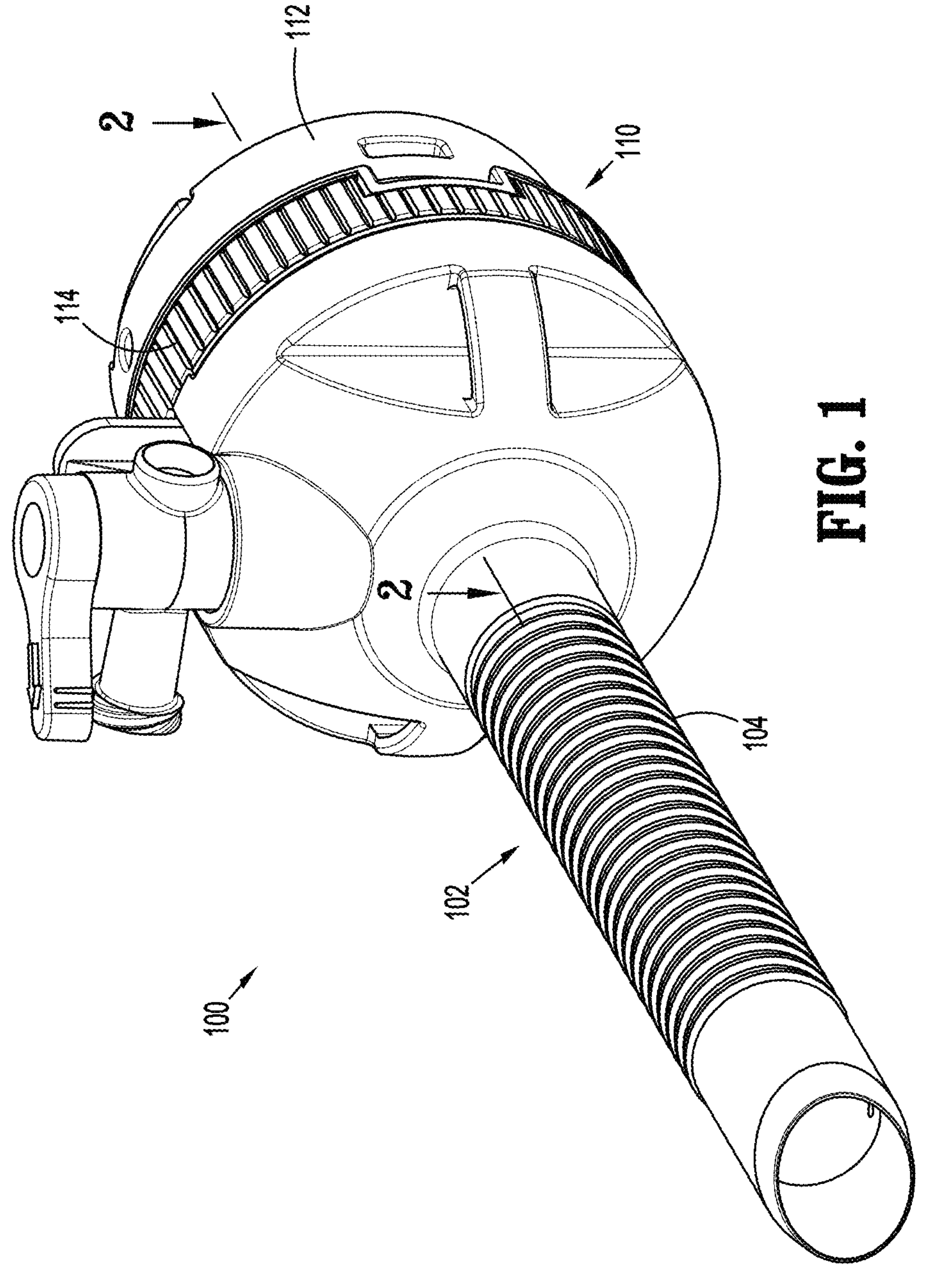
FIG. 1 is a perspective view of a surgical access assembly according to an embodiment of the present disclosure.

With initial reference now to FIG. 1, a surgical access assembly according to aspects of the present disclosure is shown generally as surgical access assembly 100. The surgical access assembly 100 includes a cannula 102 with a cannula tube 104 extending therefrom and a valve housing 110 secured to the cannula tube 104. For a detailed description of an exemplary surgical access assembly, please refer to the '905 publication.

Figure 2:
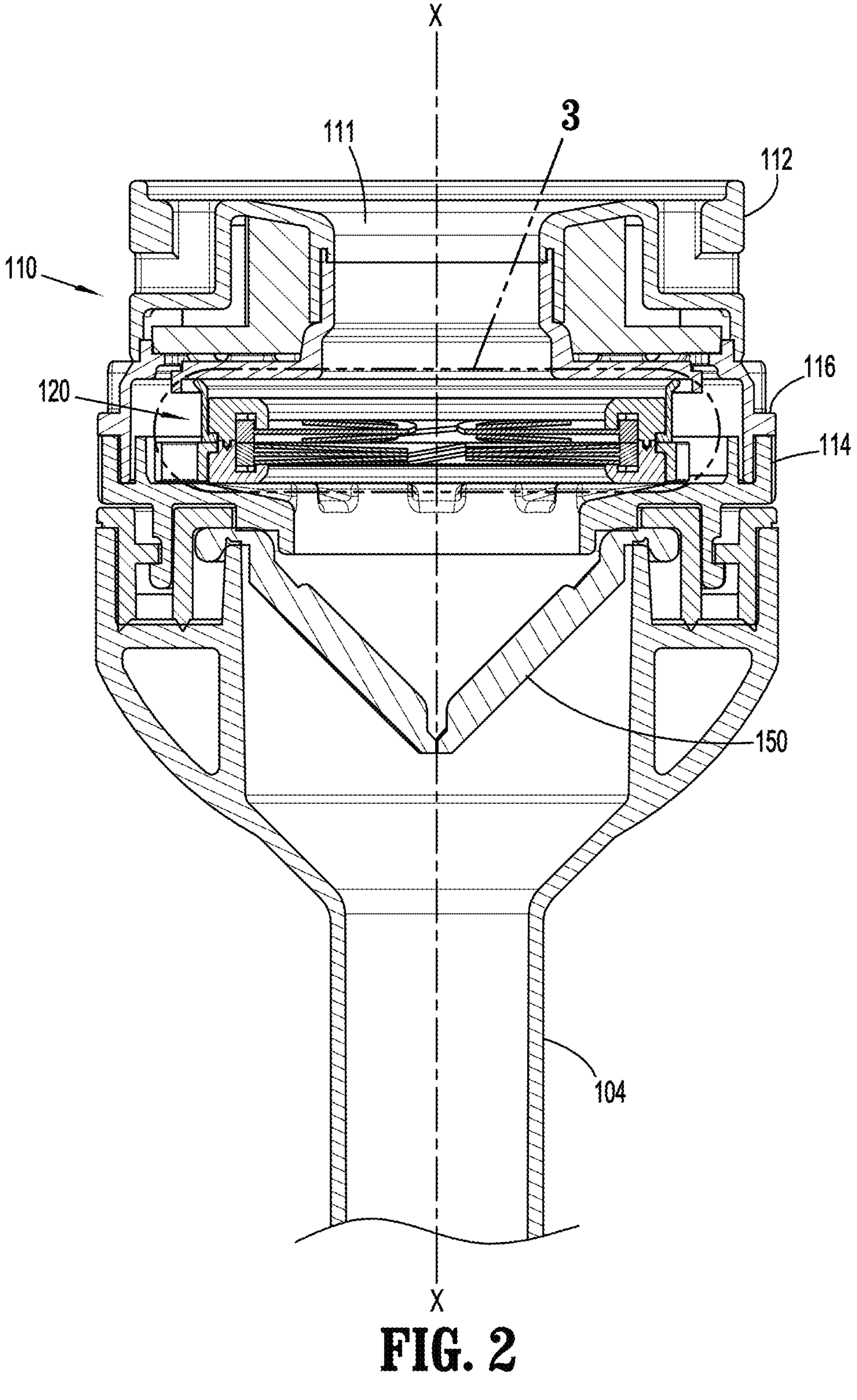
FIG. 2 is a cross-sectional view of the surgical access assembly of FIG. 1 taken along section line 2-2 of FIG. 1.

With additional reference to FIG. 2, the valve housing 110 of the surgical access assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing sections 112, 114 of the valve housing 110 may be selectively attachable to, and detachable from, the inner housing section 116. The lower housing section 114 may be releasably or permanently attached to a cannula tube 104 of the cannula assembly 102. In embodiments, either or both of the upper and lower housing sections 112, 114 of the valve housing 110 may include knurls, indentations, tabs, or be otherwise configured to facilitate engagement by a clinician.

The surgical access assembly 100 may also include features for the stabilization of the surgical access assembly. For example, the distal end of the cannula tube 104 can carry a balloon anchor or another expandable member that engages the abdomen from the interior side. For example, see U.S. Pat. No. 7,300,448, the entire disclosure of which is hereby incorporated by reference herein. A feature on the opposite side of the abdominal wall can be used to further stabilize the surgical access assembly, such as adhesive tabs or adjustable foam collars.

The upper, lower, and inner housing sections 112, 114, 116 of the valve housing 110 define a longitudinal passage 111 for receipt of a surgical instrument (not shown). The valve assembly 120 is supported within the valve housing 110 to provide sealed passage of the surgical instrument through the surgical access assembly 100. A duck-bill or zero closure seal 150 is positioned in the valve housing 110. The zero closure seal 150 is configured to prevent fluids from passing from the cannula tube 104 and proximally through the valve housing 110 in the absence of a surgical instrument positioned in the valve housing 110.

Figure 3:
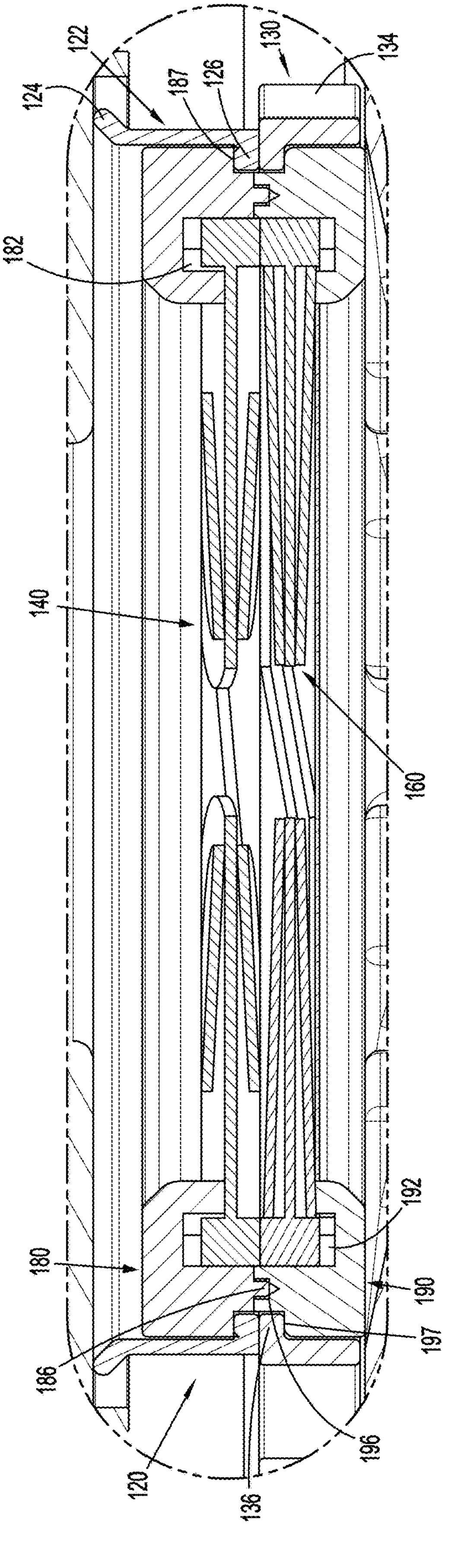
FIG. 3 is an enlarged view of the indicated area of detail of FIG. 2.
Figure 4:
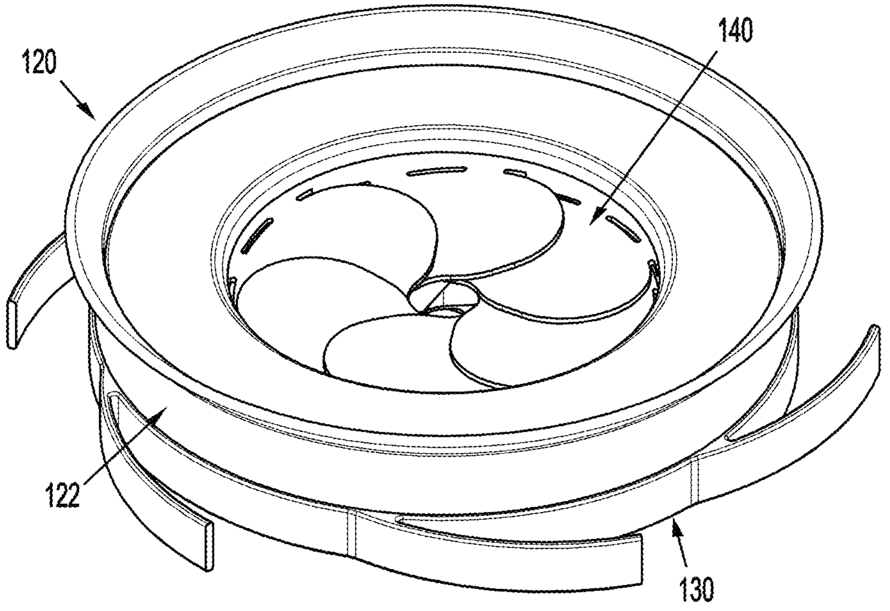
FIG. 4 is a top perspective view of a valve assembly according to an embodiment of the present disclosure.
Figure 5:
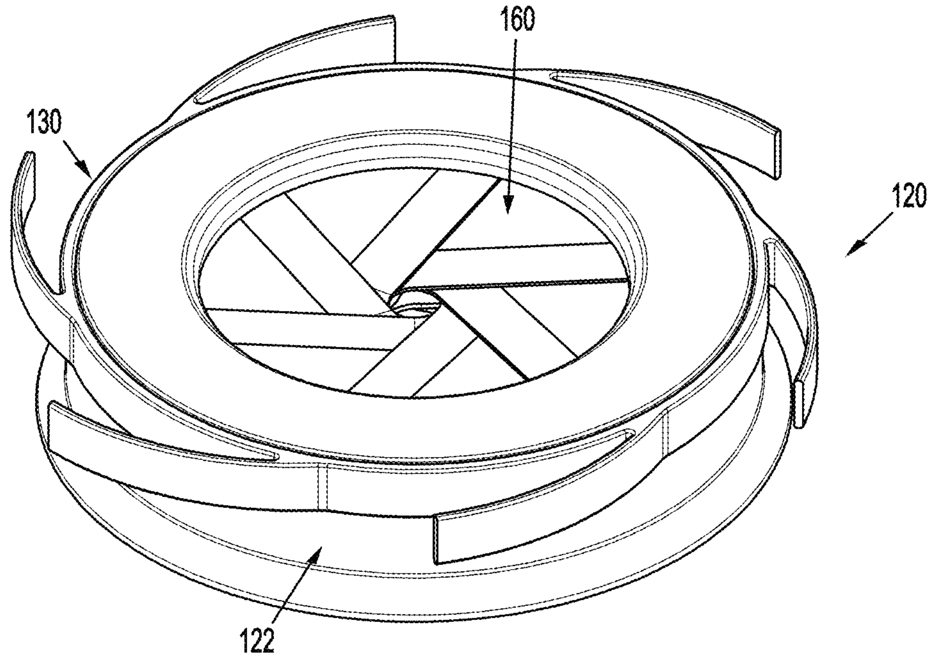
FIG. 5 is a bottom perspective view of the valve assembly of FIG. 4.

Referring now to FIG. 3, the various components of the valve assembly 120 are illustrated in their assembled configuration. The valve assembly 120 includes a ring 122, a centering mechanism 130, a guard 140, a seal 160, and first and second discs 180, 190 of a retainer 200 (FIG. 6).

Figure 6:
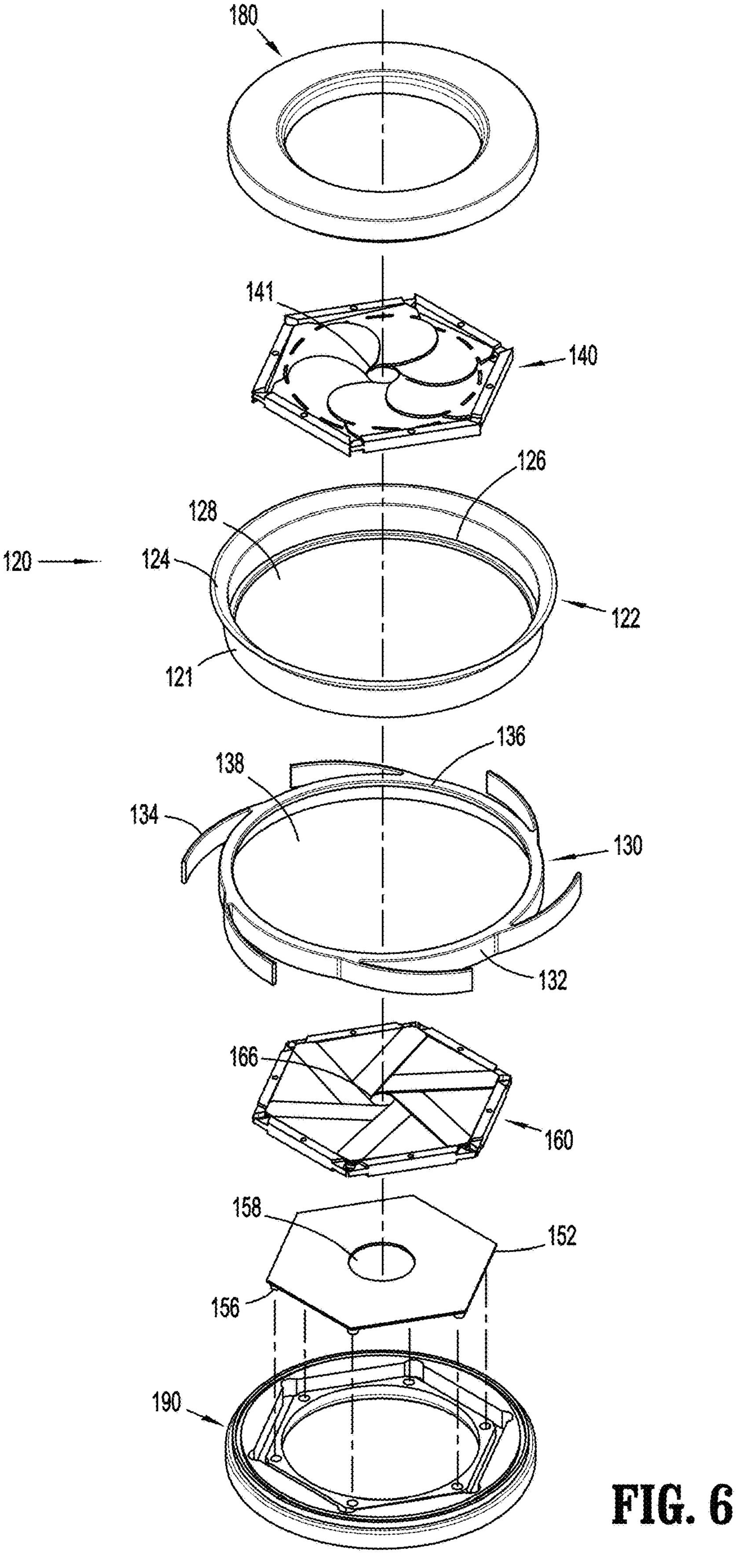
FIG. 6 is an exploded view, with parts separated, of the valve assembly of FIG. 4 including a centering mechanism, a ring, a guard, a seal, a plate, and a retainer.

With additional reference to FIG. 6, the ring 122 has a flange 124 and is located in a proximal region of the valve assembly 120. The flange 124 extends away from the ring 122 in a proximal direction and at an angle relative to the ring 122 such that a proximal end of the ring 122 has a diameter that is greater than a diameter of the distal end of the ring 122. A rim 126 extends towards a center opening 128 of the ring 122 (i.e., inboard) from a distal end of a wall 121 of the ring 122 and defines a ledge. The rim 126 is in an abutting relationship with a hoop 132 of the centering mechanism 130.

With continued reference to FIGS. 1-3 and 6, the centering mechanism 130 includes the hoop 132 and fingers 134 that are flexibly and resiliently attached to an outer surface of the hoop 132. The fingers 134 extend radially from the outer surface of the hoop 132 and are biased away from the outer surface of the hoop 132. When the centering mechanism 130 is disposed in the valve housing 110, distal portions of the fingers 134 are in contact with an inner surface of the lower housing section 114. The fingers 134 are configured to help maintain a center of the hoop 132 in coaxial alignment with a central longitudinal axis X-X of the valve housing 110. The hoop 132 is spring loaded when positioned in the valve housing 110 as all of the fingers 134 are slightly compressed towards the outer surface of the hoop 132. As the fingers 134 are compressed equally, the hoop 132 is in a state of equilibrium and its center is coaxially aligned with the central longitudinal axis X-X of the valve housing 110. When the hoop 132 is moved radially away from the central longitudinal axis X-X of the valve housing 110, some of the fingers 134 are compressed to a greater extent and some of the fingers 134 are under less compression (i.e., relaxed). This can occur when a surgical instrument is inserted through the hoop 132 and moved radially with respect to the central longitudinal axis X-X of the valve housing 110. Once the surgical instrument is removed, the fingers 134 under greater compression urge the hoop 132 back towards the central longitudinal axis X-X and towards the state of equilibrium. Additionally, the hoop 132 includes a rim 136 that extends towards an opening 138 of the hoop 132 (i.e., inboard) from a proximal end of a wall of the hoop 132 and defines a ledge. The rim 136 of the hoop 132 is in an abutting relationship with the rim 126 of the ring 122. The rim 136 of the hoop 132 and the rim 126 of the ring 122 both extend the same distance inboard.

Referring now to FIGS. 3, 7, 11, and 15, the first disc 180 and the second disc 190 of the retainer 200 are securable to each other. The first or top disc 180 has a central opening 188 and a ridge 186 that circumscribes the central opening 188. A recess 183 extends beneath a bottom surface of the first disc 180. Although shown as a hexagonal recess 183, it is contemplated that the recess 183 may have a different configuration with fewer (e.g., 4) sides or with more (e.g., 8) sides to match the configuration of the guard 140. Continuing with the hexagonal configuration, each side of the recess 183 includes a channel 182 that is configured to receive a portion of a frame 148 of the guard 140. In particular, the frame 148 includes a complementary number of sides 144*a-f* and each side 144*a-f* is insertable into one of the channels 182. This arrangement fixes the orientation between the first disc 180 and the guard 140 such that the guard 140 remains rotationally fixed relative to the first disc 180 as the sides 144*a-f* of the frame 148 are at least partially inserted into the channels 182 of the recess 183. The second or bottom disc 190 has a slot 196 that is configured to receive the ridge 186 of the first disc 180 therein. The second disc 190 also includes a hexagonal depression 193 that extends beneath a top surface of the second disc 190. Similar to the first disc 180, the second disc 190 may have a configuration with fewer sides or more sides and this configuration need not match the configuration of the first disc 180, but does match the configuration of a support 170 of the seal 160. Continuing with the hexagonal configuration, each side of the depression 193 includes a groove 192 that is configured to receive a portion of the support 170 of the seal 160. In particular, the support 170 includes a complementary number of sides 172*a-f* and each side 172*a-f* is insertable into one of the grooves 192. This arrangement fixes the orientation between the second disc 190 and the seal 160 such that the seal 160 remains rotationally fixed relative to the second disc 190 as the sides 172*a-f* of the support 170 are at least partially inserted into the grooves 192 of the depression 193. Additionally, the depression 193 includes receptacles 194 that are configured to accept protrusions 156 of a plate 152 (FIG. 6). The engagement between the protrusions 156 of the plate 152 and the receptacles 194 of the second disc 190 couple the plate 152 to the second disc 190 and maintains a fixed orientation between them. By using protrusions 156 on the plate 152 and receptacles 194 in the second disc 190, the orientation between the plate 152 and the second disc 190 is limited to a fixed number of orientations. The plate 152 helps support the seal 160 and limits the flexion of petals 162*a-f* of the seal 160 towards the cannula tube 104 when a surgical instrument (not shown) is inserted through the seal degrees.

Referring now to FIGS. 3, 4, 6, and 15, the guard 140 includes the frame 148 that has six sides 144*a-f*. As described hereinabove, the frame 148 may include fewer sides (e.g., 4) or more sides (e.g., 8) provided that the number of sides 144 corresponds to the number of channels 182 in the first disc 180. Each side 144*a-f* includes a bar 145*a-f* that is generally rectangular and extends along a majority of a length of the corresponding flap 142*a-f*. Each block 146*a-f* extends from one end of the bar 145*a-f* of the corresponding side 144*a-f*. Each block 146*a-f* is positioned midway between top and bottom surfaces of the bar 145*a-f* and extends parallel to the top and bottom surfaces of the bar 145*a-f*. Each bar 145*a-f* is configured to be received in the corresponding channel 182 of the recess 183 of the first disc 180 thereby fixing the relative orientations of the guard 140 with respect to the first disc 180. As assembled, the bottom surfaces of the bars 145*a-f* are substantially flush with a bottom surface of the first disc 180. Further, with the guard

140 positioned in the recess 183 of the first disc 180, the first disc 180 is disposed in the center opening 128 of the ring 122.

Figure 8:
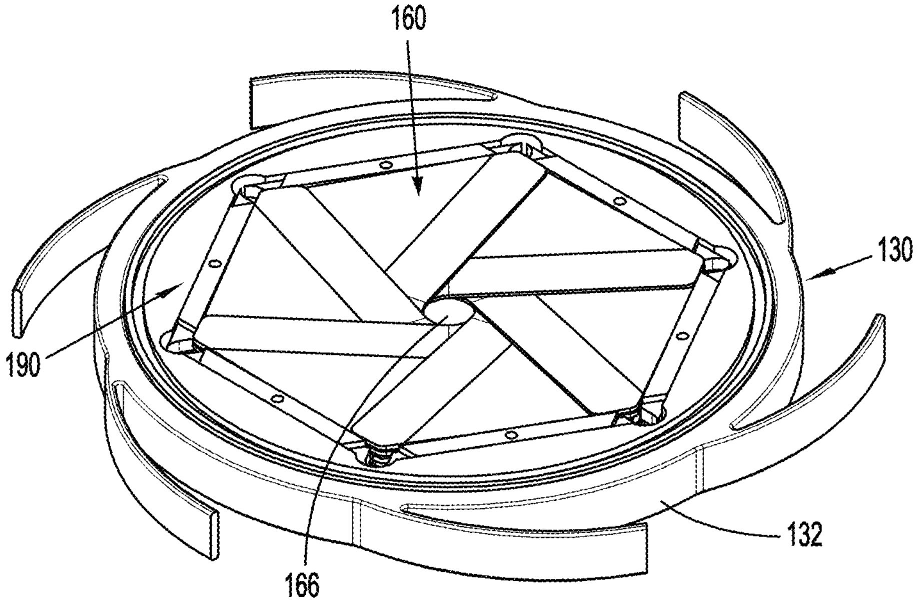
FIG. 8 is a top perspective view of the seal of FIG. 6 disposed in the bottom disc of the retainer of FIG. 6 and the bottom disc is disposed in a hoop of the centering mechanism of FIG. 6.
Figure 11:
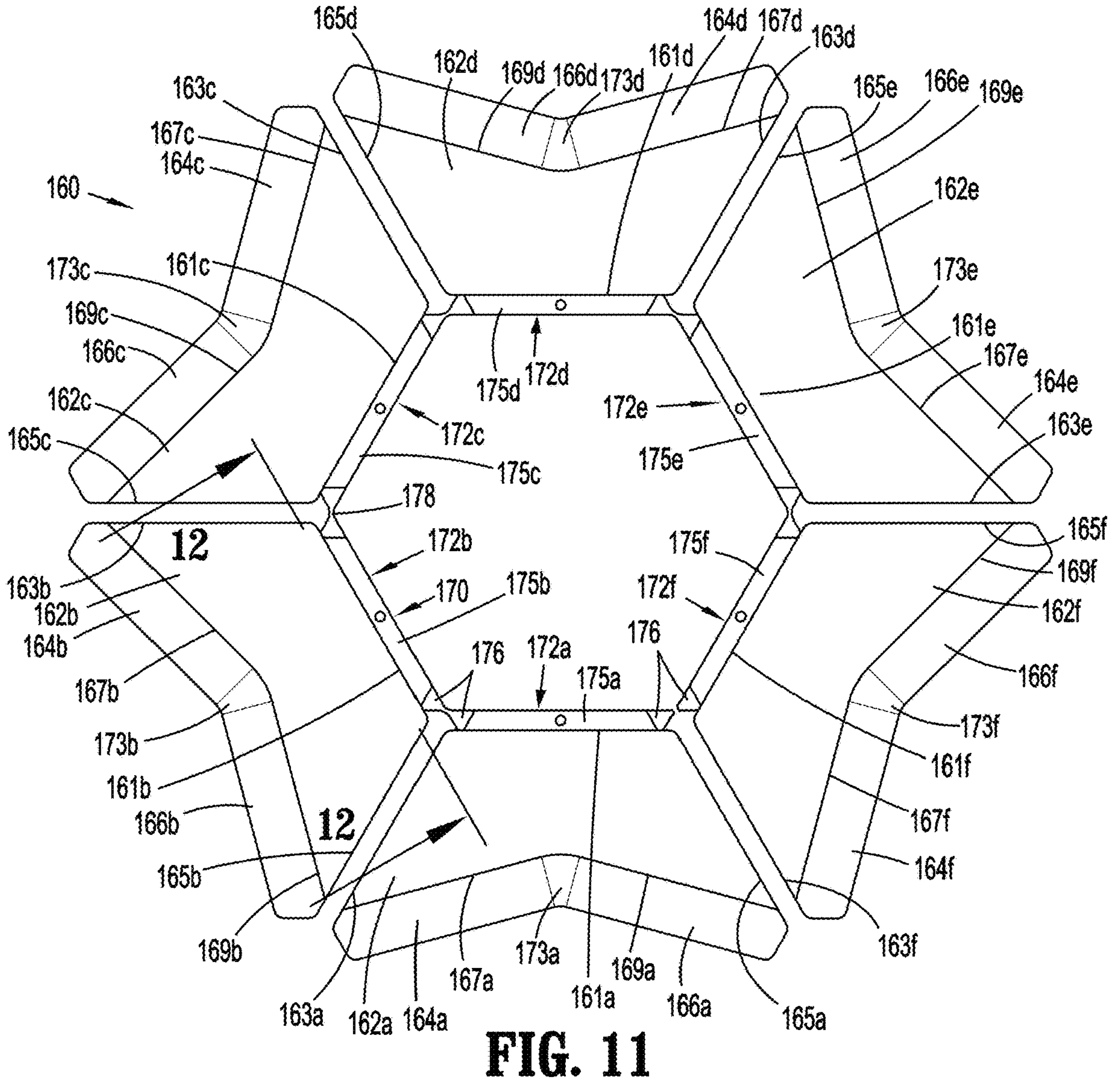
FIG. 11 is a top plan view of the seal of FIG. 10.

With additional reference to FIGS. 8 and 11, the seal 160 is illustrated with a support 170 having six sides 172*a-f*. As described hereinabove, the support 170 may include fewer sides (e.g., 4) or more sides (e.g., 8) provided that the number of sides 172 corresponds to the number of grooves 192 in the second disc 190. Each side 172*a-f* includes a beam 175*a-f* that is generally rectangular and extends along a majority of a length of the corresponding petal 162*a-f*. Wedges 176 extend from opposing ends of each beam 175*a-f*. Each wedge 176 is positioned midway between top and bottom surfaces of the beam 175*a-f* and extends parallel to the top and bottom surfaces of the beam 175*a-f*. As will be described in further detail below, the wedges 176 are joined to form living hinges 178. Each beam 175*a-f* is configured to be received in the corresponding groove 192 of the depression 193 of the second disc 190 thereby fixing the relative orientations of the seal 160 with respect to the second disc 190. As assembled, the top surfaces of the beams 175*a-f* are substantially flush with a top surface of the second disc 190. Further, with the seal 160 positioned in the depression 193 of the second disc 190, the second disc 190 is disposed in the opening 138 of the hoop 132.

Figure 7:
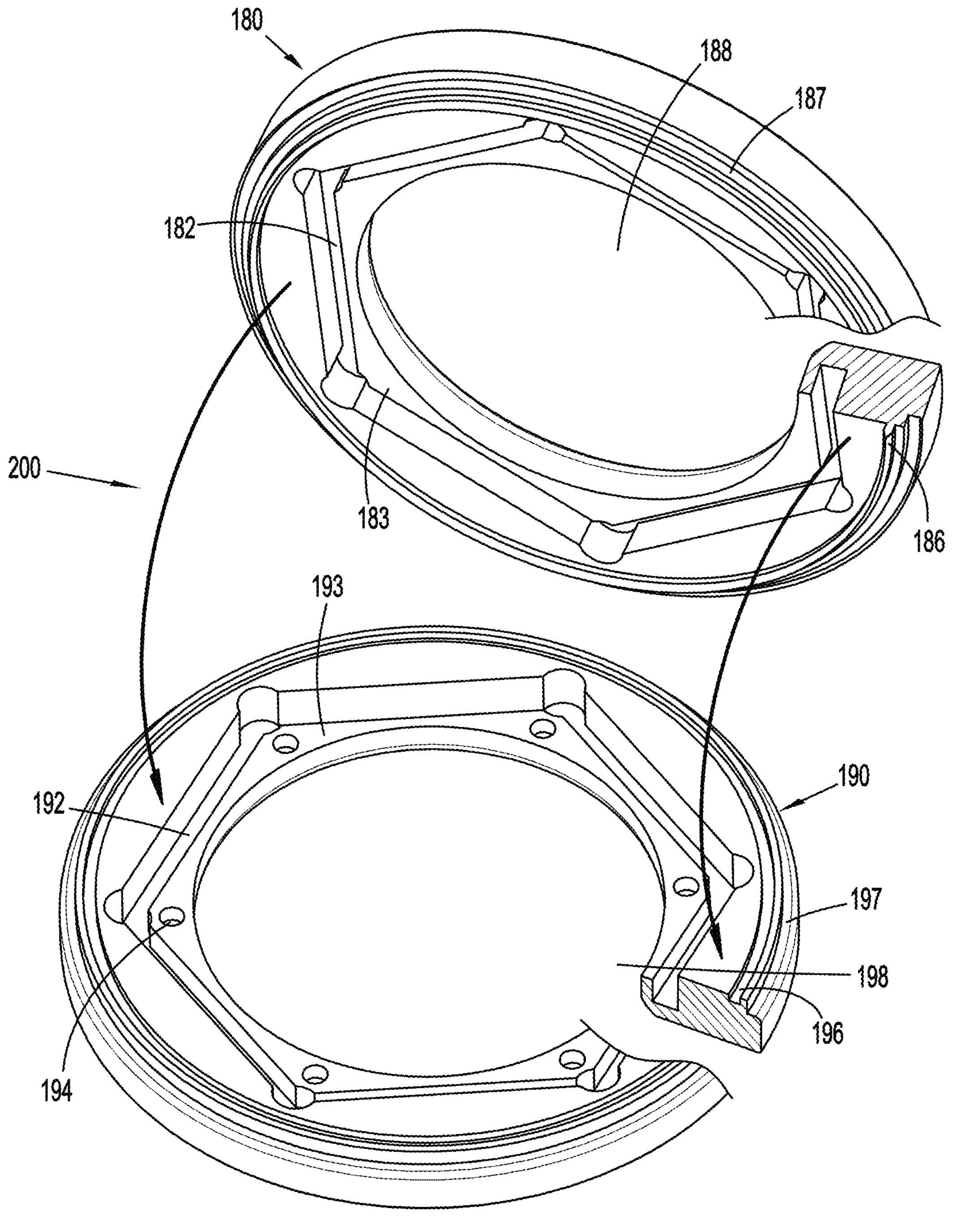
FIG. 7 is a bottom perspective view of a top disc of the retainer of FIG. 6 and a top perspective view of a bottom disc of the retainer of FIG. 6.
Figure 9:
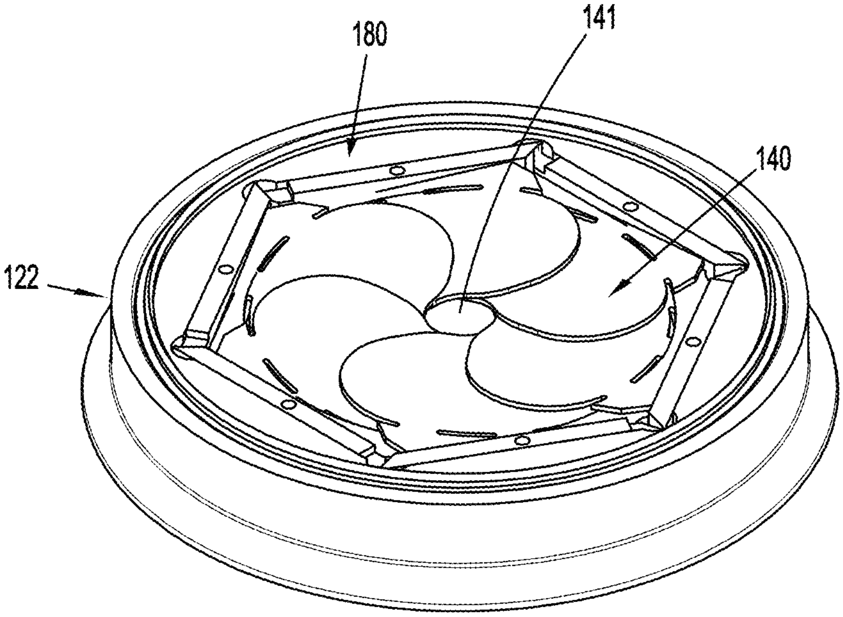
FIG. 9 is a bottom perspective view of the guard of FIG. 6 disposed in the top disc of the retainer of FIG. 6 and the top disc is disposed in the ring of FIG. 6.

Referring now to FIGS. 3, 8, and 9, the first disc 180 with the guard 140 installed therein is positioned in the ring 122 and the second disc 190 with the seal 160 installed therein is positioned in the hoop 132. As seen in FIGS. 3 and 7, the first disc 180 has a notch 187 at its distal end that circumscribes the first disc 180. The notch 187 is configured to complement the rim 126 of the ring 122 and support the first disc 180 in the opening 128 of the ring 122. The rim 126 provides a limit stop on movement of the first disc 180 through the ring 122 in a distal direction. It is contemplated that an outer diameter of the first disc 180 and an inner diameter of the ring 122 may be sized such that the first disc 180 is retained within the opening 128 of the ring 122 by frictional engagement between the outer surface of the first disc 180 and an inner surface of the ring 122. Similarly, the second disc 190 also includes a notch 197 at its proximal end that circumscribes the second disc 190. The notch 197 is configured to complement the ledge 136 of the hoop 132 and limit the proximal travel of the second disc 190 through the hoop 132. It is contemplated that an outer diameter of the second disc 190 and an inner diameter of the hoop 132 may be sized such that the second disc 190 is retained within the hoop 132 by frictional engagement between the outer surface of the second disc 190 and an inner surface of the hoop 132. With the first disc 180 fully seated in the ring 122 and the second disc 190 fully seated in the hoop 132, placing the ring 122 and the hoop 132 are in an abutting relationship results in the bottom surface of the first disc 180 resting atop the top surface of the second disc 190. Further still, the ridge 186 that extends from the bottom surface of the first disc 180 enters the slot 196 that extends into the top surface of the second disc 190, thereby coupling the first and second discs 180, 190 as well as the ring 122 and the hoop 132.

As the ridge 186 of the first disc 180 and the slot 196 of the second disc 190 extend continuously around central openings 188, 198 of the respective first and second discs 180, 190, the first disc 180 can be attached to the second disc 190 in a multitude of orientations rather than a discrete number of orientations that would be defined by a complementary arrangement of posts and receptacles as seen with the fixation arrangement of the plate 152 and the second disc 190. Additionally, by using the ridge 186 and slot 196 arrangement between the first and second discs 180, 190, the orientation between the guard 140 and the seal 160 is easily adjustable prior to securing the first and second discs 180, 190 together. This simplifies the assembly of the valve assembly 120 and assists in orienting the guard 140 and seal 160 prior to securing the first and second discs 180, 190 together. Once the desired orientation between the guard 140 and seal 160 is achieved, the first disc 180 is welded to the second disc 190. Welding the first and second discs 180, 190 together provides a fluid tight seal between the first and second discs 180, 190. It is contemplated that the first and second discs 180, 190 may be secured to each other using an adhesive. It is also contemplated that the first disc 180 may include a slot and the second disc 190 may include a ridge.

Figure 10:
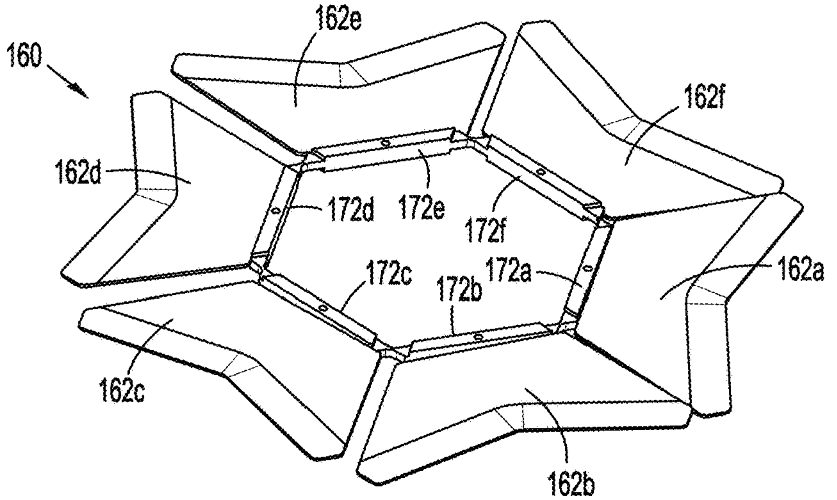
FIG. 10 is a top perspective view of the seal of FIG. 6 in an unfolded configuration.
Figure 12:
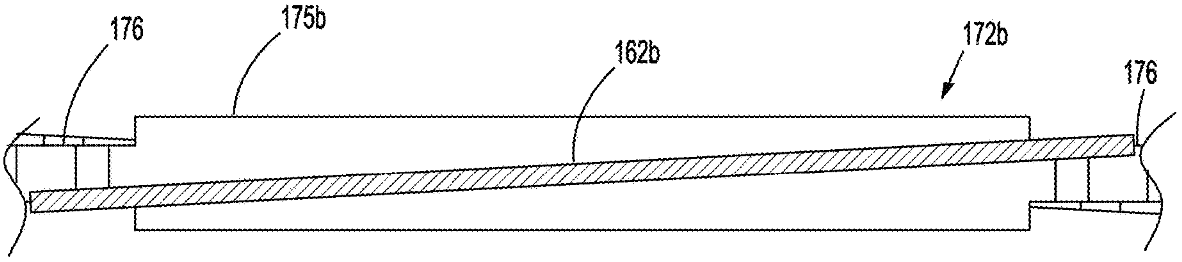
FIG. 12 is an end cross-sectional view of a petal of the seal taken along section line 12-12 of FIG. 11.
Figure 13:
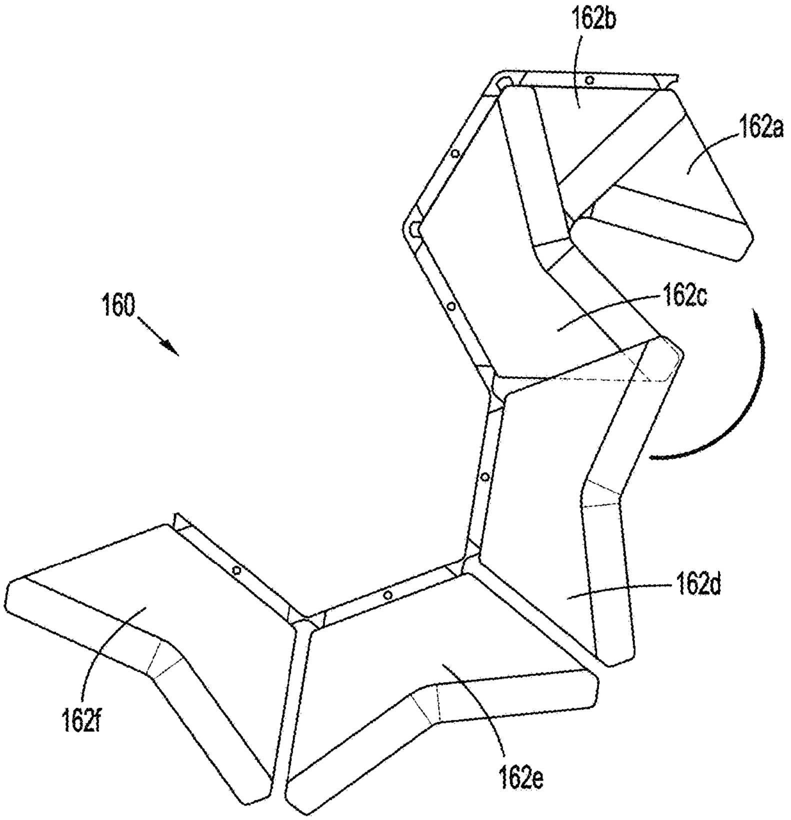
FIG. 13 is a top plan view of the seal of FIG. 10 showing the folding sequence of the petals.

Referring now to FIGS. 10-14, the sequence of steps for transforming the seal 160 from an unfolded configuration (FIG. 10) to a folded configuration (FIG. 14) is illustrated. Initially, as seen in FIGS. 10 and 11, the seal 160 is in the unfolded configuration. Each beam 175*a-f* is connected to an adjacent beam 175*a-f* with one exception. As shown in FIG. 11, one of the wedges 176 of the first petal 162*a* is spaced apart from one of the wedges of the sixth petal 162*f* defining a gap therebetween while the remaining wedges 176 are connected to each other. A living hinge 178 is formed where the wedges 176 are connected to each other. Additionally, as seen in FIG. 12, each petal 162*a-f* is angled with respect to the top and bottom surfaces of the corresponding beam 175*a-f*. This angled arrangement in conjunction with the gap between the wedges 176 of the first and sixth petals 162*a*, 162*f* facilitates folding and unfolding of the seal 160 as will be discussed hereinbelow. Each petal 162*a-f* is connected to a corresponding beam 175*a-f* of the support 170 along a first or connection side 161*a-f*. Each petal 162*a-f* also includes angled second and third sides 163*a-f*, 165*a-f* that extend from the corresponding connection side 161*a-f* in a divergent manner. Fourth and fifth sides 167*a-f*, 169*a-f* of each petal 162*a-f* interconnect the angled second and third sides 163*a-f*, 165*a-f*. The fourth and fifth sides 167*a-f*, 169*a-f* of the petals 162*a-f* have equal lengths and are angled towards the corresponding connection side 161*a-f* such that they meet at a point that would bisect the connection side 161*a-f*. The fourth and fifth sides are oriented such that they that they define an angle of 150°. The fourth and fifth sides may define an angle between about 120° and about 165°. First and second extenders 162*a-f*, 164*a-f* are attached to the fourth and fifth sides 167*a-f*, 169*a-f*. The first and second extenders 162*a-f*, 164*a-f* have equal lengths and meet at a taper 173*a-f* that also is located at a point that would bisect the corresponding connection side 161*a-f*.

Figure 14:
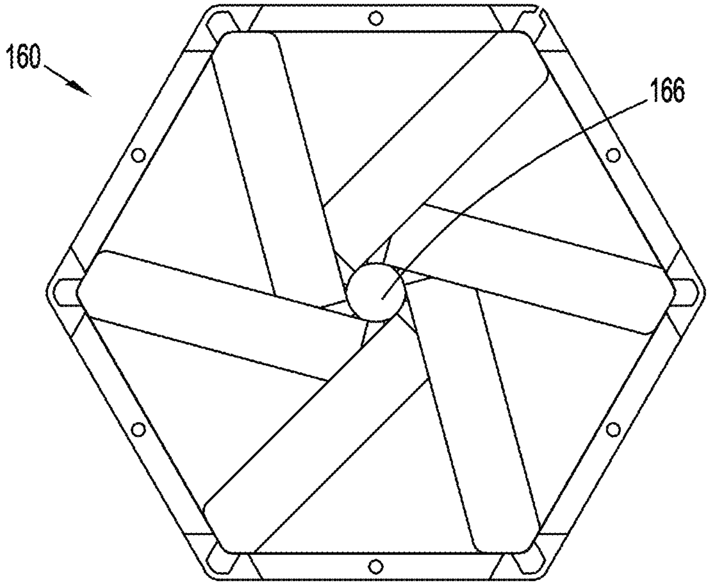
FIG. 14 is a top plan view of the seal of FIG. 10 in a fully folded configuration.

The wedges 176 of the first through fifth beams 175*a-e* are connected to the wedges 176 of the second through sixth beams 175*b-f* defining five living hinges 178 with a gap existing between the first beam 175*a* and the sixth beam 175*f*. Since the wedge 176 of the first beam 175*a* is not connected to the wedge 176 of the sixth beam 175*f*, the first beam 175*a* and the first petal 162*a* can be repositioned without disturbing the position of the sixth beam 175*f* and the sixth petal 162*f*. The first petal 162*a* is folded by pivoting the first beam 175*a* and the first petal 162*a* about a point defined by the living hinge 178 that is disposed between the first and second beams 175*a*, 175*b*. As such, the first petal 162*a* partially overlaps the second petal 162*b*. Subsequently, the first and second petals 162*a*, 162*b* are pivoted by pivoting the second beam 175*b* about the living hinge 178 formed between the second beam 175*b* and the third beam 175*c* such that the second petal 162*b* partially overlaps the third petal 162*c*. Next, the first, second, and third petals 162*a-c* are pivoted by pivoting the third beam 175*c* about the living hinge 175 formed between the third beam 175*c* and the fourth beam 175*d* such that the third petal 162*c* partially overlaps the fourth petal 162*d*. Subsequently, the first, second, third, and fourth petals 162*a-d* are pivoted by pivoting the fourth beam 175*d* about the living hinge 178 formed between the fourth beam 175*d* and the fifth beam 175*e* such that the fourth petal 162*d* partially overlaps the fifth petal 162*c*. The first, second, third, fourth, and fifth petals 162*a-e* are pivoted by pivoting the fifth beam 175*c* about the living hinge 178 formed between the fifth beam 175*e* and the sixth beam 175*f* such that the fifth petal 162*e* partially overlaps the sixth petal 162*f* and the sixth petal 162*f* partially overlaps the first petal 162*a*. The fully folded seal 160 is illustrated in FIG. 14.

After all the petals 162*a-f* are folded, a center orifice 166 is defined and is configured to engage an outer surface of a surgical instrument inserted through the seal 160 such that the center orifice 166 surrounds the surgical instrument in a sealing manner to inhibit the passage of insufflation fluids and define a fluid tight barrier. As each petal 162*a-f* at least partially overlaps a first adjacent petal 162 and is at least partially overlapped by a second adjacent petal 162, the petals 162*a-f* of the seal are interwoven. This interwoven arrangement of the petals 162*a-f* facilitates the seal 160 maintaining its shape during insertion and withdrawal of a surgical instrument through the center orifice 166. For example, with additional reference to FIGS. 2 and 3, during insertion of the surgical instrument through the valve housing 110 of the surgical access assembly 100, a shaft of the surgical instrument passes through the central opening 188 of the first disc 188, a center bore 141 of the guard 140, the center orifice 166 of the seal 160, and the central opening 198 of the second disc 190. As the shaft of the surgical instrument passes through the center orifice 166 of the seal 160 during insertion, the petals 162*a-f* of the seal 160 flex towards the second disc 190 and surround an outer surface of the shaft of the surgical instrument providing a fluid tight barrier between the petals 162*a-f* of the seal 160 and the shaft of the surgical instrument. During withdrawal of the surgical instrument, the petals 162*a-f* of the seal 160 flex towards a proximal portion of the valve housing 110 in response to proximal movement of the shaft of the surgical instrument. The petals 162*a-f* of the seal 160 resiliently return to their initial or rest configuration (FIG. 3) once the shaft of the surgical instrument is removed from the center orifice 166 of the seal 160. Due to the petals 162*a-f* being interwoven, they return to the initial configuration. In the event that the petals 162*a-f* have slightly different rates of movement, the interwoven arrangement of the petals 162*a-f* results in the slowest moving petal 162 acting as a governor and limiting the rate of movement of the remaining petals 162. This tends to maintain contact between the petals 162*a-f* and the outer surface of the shaft of the surgical instrument thereby maintaining the fluid tight boundary of the seal 160 with respect to the surgical instrument during movement of the shaft relative to the seal 160.

Referring now to FIGS. 15-18, the guard 140 of the valve assembly 120 is illustrated. The guard 140 helps protect the seal 160 during insertion and withdrawal of the surgical instrument through the valve assembly 120. The central opening 141 of the guard 140 has a diameter that is greater than the outer diameter of the shaft of the surgical instrument. During insertion of the surgical instrument through the valve assembly 120, the shaft of the surgical instrument passes through the central opening 141 of the guard 140. As the diameter of the central opening 141 is greater than the diameter of the shaft of the surgical instrument, the shaft may pass through the central opening 141 without contacting any flaps 142*a-f* of the guard 140. In instances where the shaft is off axis from a central longitudinal axis of the guard 140 or the shaft is inserted at an angle relative to the central longitudinal axis, the tip of the shaft contacts one or more flaps 142*a-f* of the guard 140 as the shaft moves through the central opening 141 of the guard 140. The central longitudinal axis of the guard 140 is coaxially aligned with the central longitudinal axis X-X of the valve housing 110 (FIG. 2). The flap or flaps 142*a-f* of the guard 140 act to reduce any impact force from the tip of the shaft that would be transmitted to the seal 160. This helps maintain the integrity and lifespan of the seal 160 such that the seal 160 is capable of enduring multiple insertions of the surgical instrument without damage from the surgical instrument.

Figure 15:
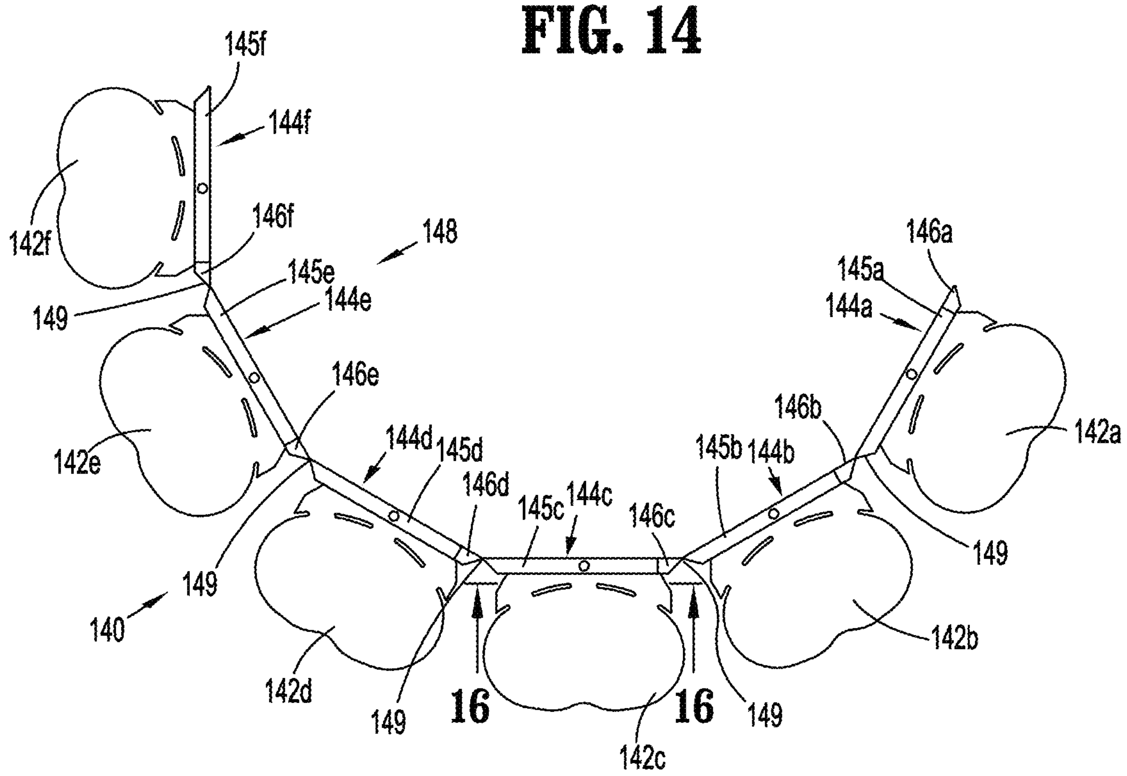
FIG. 15 is a top plan view of the guard of FIG. 6 in an unfolded configuration.
Figure 16:
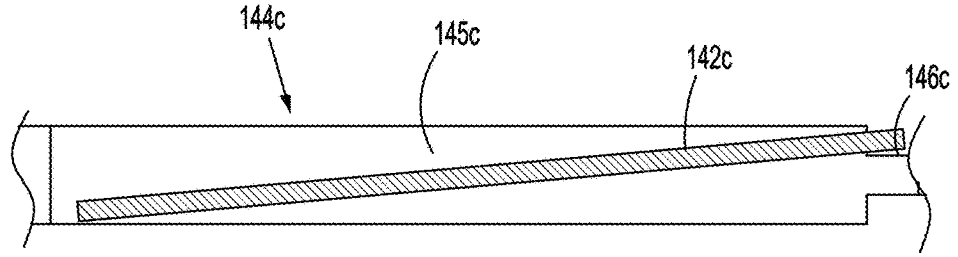
FIG. 16 is an end cross-sectional view of a flap of the guard taken along section line 16-16 of FIG. 15.
Figure 17:
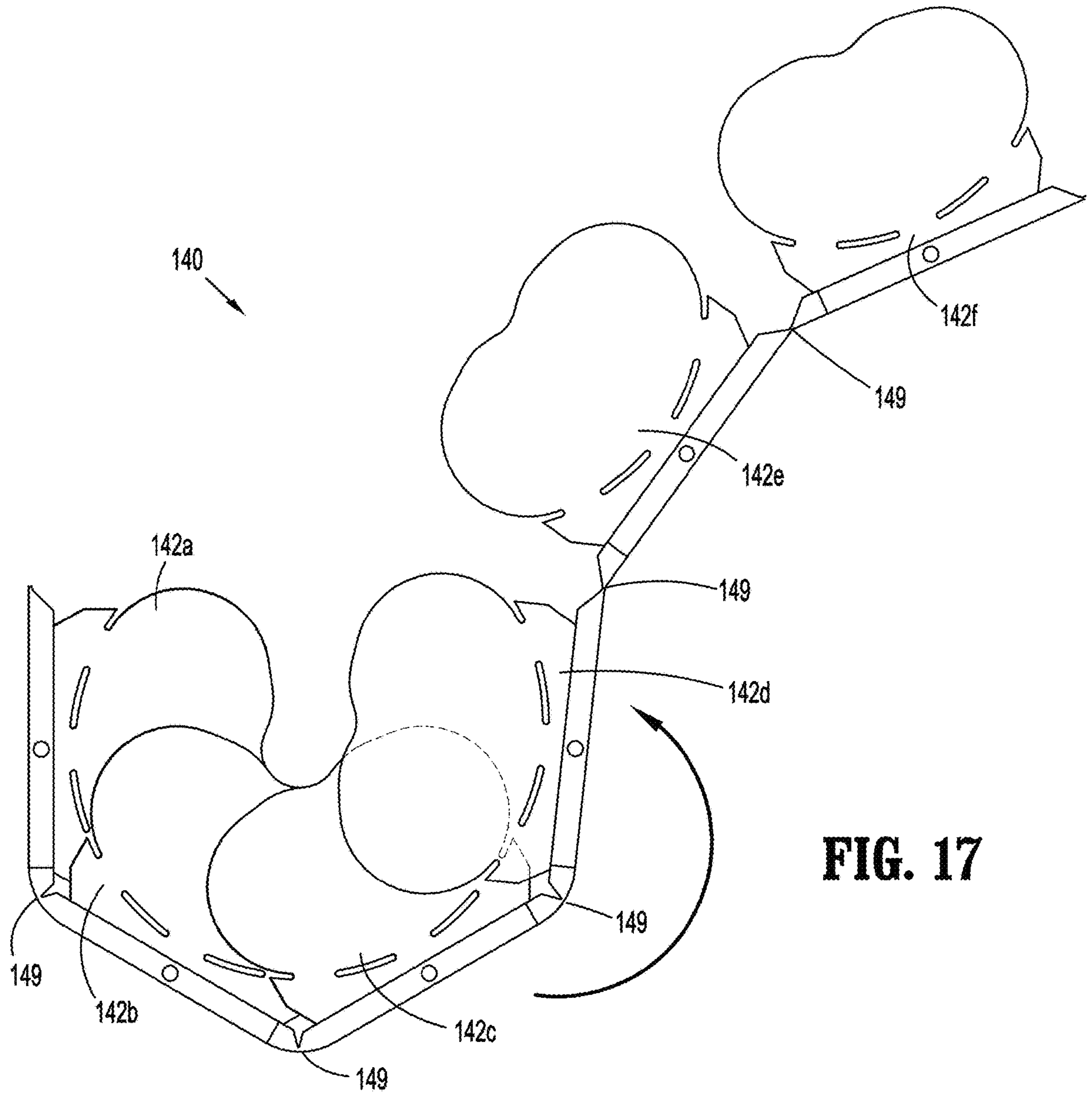
FIG. 17 is a top plan view of the guard of FIG. 15 showing the folding sequence of the flaps.

In particular, the guard 140 includes the flaps 142*a-f* that are attached to a multi-sided frame 148. As illustrated in FIG. 15, the guard 140 includes a six-sided frame 148 with six flaps 142*a-f* where each flap 142*a-f* is flexibly and resiliently attached to one side 145*a-f* of the frame 148. The frame 148 may include fewer sides 145 (e.g., 4) or more sides 145 (e.g., 8) provided that the number of sides 145 corresponds to the number of channels 182 present in the recess 183 of the first disc 180. Each side 145*a-f* of the frame 148 is a generally trapezoidal configuration. Similar to the support 170 of the seal 160, the sides 145-*a-f* of the frame 148 are joined to one another with the exception of two of the sides 145*a*, 145*f* (FIG. 15). Each side 145*a-f* of the frame 148 has a block 146*a-f* at one end of the side 14*a-f*. The blocks 146*a-e* of the first through fifth sides 145*a-e* are connected to the second through sixth sides 145*b-f* defining five living hinges 149. Since the block 146*a* of the first side 145*a* is not connected to the sixth side 145*f*, the first side 145*a* and the first flap 142*a* can be repositioned without disturbing the position of the sixth side 145*f* and the sixth flap 142*f*. This allows folding of the guard 140 as will be explained hereinbelow. Additionally, as seen in FIG. 16, each flap 142*a-f* is angled with respect to the top and bottom surfaces of the corresponding side 145*a-f*. This angled arrangement in conjunction with the gap between the first side 145*a* and the sixth side 145*f* facilitates folding and unfolding of the guard 140 as will be discussed hereinbelow.

Figure 18:
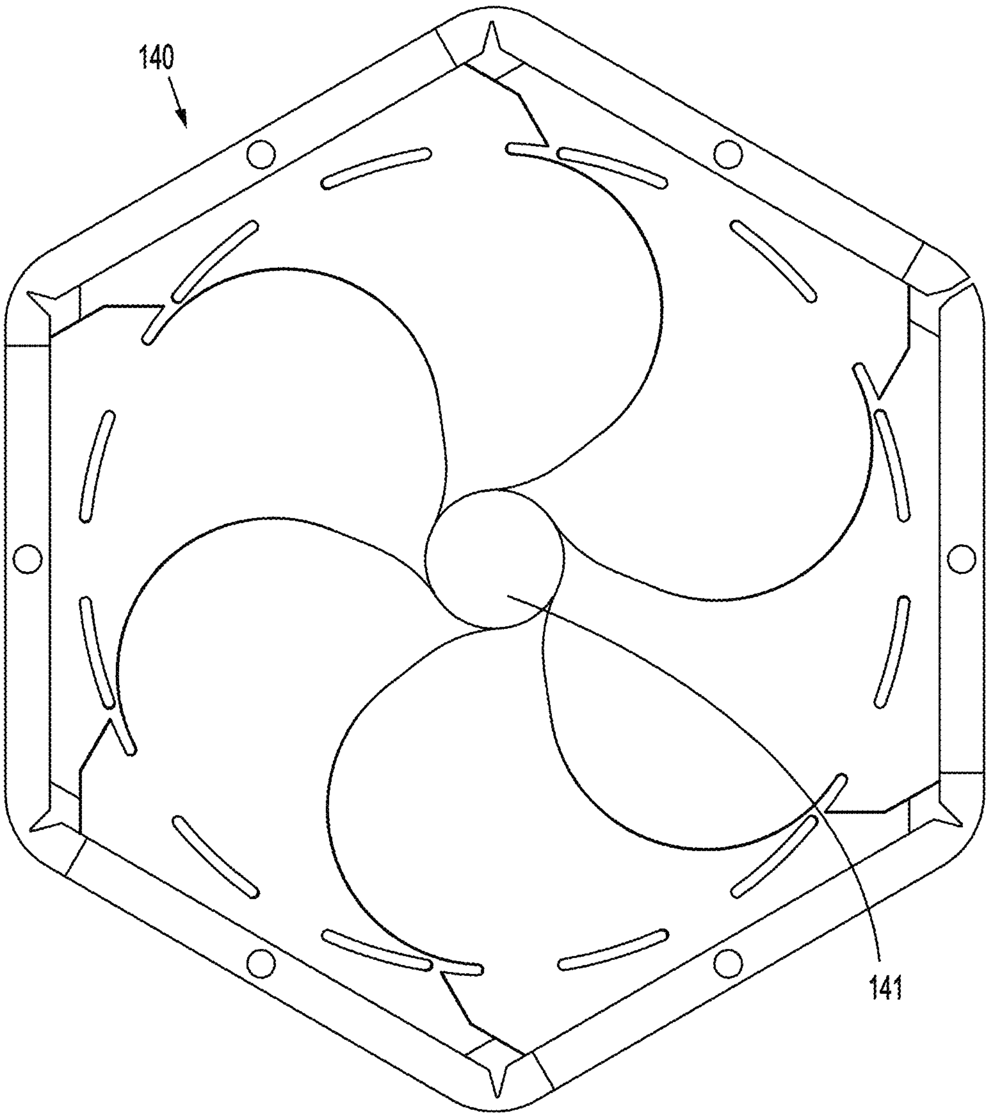
FIG. 18 is a top plan view of the guard of FIG. 15 in a fully folded configuration.

With the guard 140 in an initial, unfolded configuration (FIG. 15), the first flap 142*a* is folded by pivoting the first side 145*a* and the first flap 142*a* about a point defined by the living hinge 149 that is disposed between the first and second sides 145*a*, 145*b*. As such, the first flap 142*a* partially overlaps the second flap 142*b*. Subsequently, the first and second flaps 142*a*, 142*b* are pivoted by pivoting the second side 145*b* about the living hinge 149 formed between the block 146*b* of the second side 145*b* and the third side 145*c* such that the second flap 142*b* partially overlaps the third flap 142*c*. Next, the first, second, and third flaps 142*a-c* are pivoted by pivoting the third side 145*c* about the living hinge 149 formed between the block 146*c* of the third side 145*c* and the fourth side 145*d* such that the third flap 142*c* partially overlaps the fourth flap 142*d*. Subsequently, the first, second, third, and fourth flaps 142*a-d* are pivoted by pivoting the fourth side 145*d* about the living hinge 149 formed between the block 149*d* of the fourth side 145*d* and the fifth side 145*e* such that the fourth flap 142*d* partially overlaps the fifth flap 142*c*. The first, second, third, fourth, and fifth flaps 142*a-e* are pivoted by pivoting the fifth side 145*c* about the living hinge 149 formed between the block 146*e* of the fifth side 145*e* and the sixth side 145*f* such that the fifth flap 142*e* partially overlaps the sixth flap 142*f* and the sixth flap **142*f* partially overlaps the first flap 142*a*. The fully folded guard 140 is illustrated in FIG. 18**.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A surgical access assembly comprising:

a housing;

a contoured disc seated in the housing, the disc comprising a center opening;

a guard mated with the contoured disc, the guard comprising a plurality of flaps that overlap around a center bore;

a seal positioned in the housing distally of the guard, the seal comprising a plurality of petals that overlap around a center orifice, wherein the center opening of the disc, the center bore of the guard, and the center orifice of the seal are aligned along an axis; and a hoop surrounding the seal, wherein the hoop is spring-loaded in the housing via a plurality of fingers in contact with the housing and compressed toward the hoop, the plurality of fingers urging the hoop into alignment with the axis.

2. The surgical access assembly of claim 1, wherein the disc comprises a recess on a proximal-facing side of the disc, and a portion of the guard is received into the recess of the contoured disc.

3. The surgical access assembly of claim 1, wherein the housing comprises an upper housing section and a lower housing section, and wherein a distal portion of each finger of the fingers is in contact with an inner surface of the lower housing section.

4. The surgical access assembly of claim 1, wherein the seal further comprises an inner support, and wherein each petal of the plurality of petals is connected to the inner support.

5. The surgical access assembly of claim 4, wherein each petal of the plurality of petals comprises two lateral sides that diverge from the inner support.

6. The surgical access assembly of claim 5, wherein each petal of the plurality of petals further comprises two angled that meet at an angle that bisects the petal.

7. The surgical access assembly of claim 1, wherein the plurality of fingers extend radially outward from the hoop.

8. The surgical access assembly of claim 1, wherein the center bore of the guard comprises a first diameter and the center orifice of the seal comprises a second diameter, and wherein the first diameter is greater than the second diameter.

9. The surgical access assembly of claim 1, wherein the plurality of fingers are flexibly coupled to an outer surface of the hoop.

10. The surgical access assembly of claim 9, wherein the plurality of fingers are compressed by the housing.

11. The surgical access assembly of claim 1, wherein the plurality of petals flex in a proximal direction in response to proximal movement of a surgical instrument.

12. A surgical access assembly comprising:

a housing comprising a central longitudinal axis;

a seal assembly received within the housing and comprising:

a first disc comprising a proximally-facing surface;

a guard positioned against the proximally-facing surface, the guard comprising a plurality of curved flaps that fold into a first overlapping configuration around a center bore;

a seal positioned distally of the guard and comprising a plurality of petals that fold into a second overlapping configuration around a center orifice, and a second disc attached to the first disc with the guard and the seal captured between the first disc and the second disc with the center bore and the center orifice aligned with the central longitudinal axis; and a hoop spring-loaded into the housing, the hoop surrounding the seal assembly and comprising a plurality of fingers urging the hoop into alignment with the central longitudinal axis.

13. The surgical access assembly of claim 12, wherein the first disc and the second disc comprise a mating interface comprising a ridge and a slot.

14. The surgical access assembly of claim 12, wherein the first disc and the second disc are attachable irrespective of the rotational orientation of the first disc relative to the second disc.

15. The surgical access assembly of claim 12, wherein the plurality of petals flex in response to proximal or distal movement of a surgical instrument.

16. The surgical access assembly of claim 12, wherein the plurality of petals comprise a geometric shape having sides that meet at an angle between about 120° and about 165°.

17. A surgical access assembly comprising:

a cannula;

a housing mounted at a proximal end of the cannula and comprising a central longitudinal passage;

a closure seal inside the housing; and a valve assembly inside the housing proximal of the closure seal, the valve assembly comprising:

an upper disc comprising a proximally-facing surface;

a guard positioned against the proximally-facing surface, the guard comprising a plurality of curved flaps that fold into a first overlapping configuration around a center bore;

a seal positioned distally of the guard and comprising a plurality of petals that fold into a second overlapping configuration around a center orifice, and a lower disc attached to the upper disc with the guard and the seal captured between the upper disc and the lower disc with the center bore and the center orifice aligned with the central longitudinal axis;

a ring surrounding the upper disc; and a hoop surrounding the valve assembly and comprising a plurality of fingers urging the hoop into alignment with the central longitudinal axis.

* * * * *